(12) United States Patent
Blank et al.

(10) Patent No.: US 10,231,670 B2
(45) Date of Patent: Mar. 19, 2019

(54) PROXIMITY SENSOR IN PULSE OXIMETER

(71) Applicant: Masimo Corporation, Irvine, CA (US)

(72) Inventors: Thomas B. Blank, Laguna Beach, CA (US); Gregory A. Olsen, Lake Forest, CA (US); Cristiano Dalvi, Lake Forest, CA (US); Hung T. Vo, Fountain Valley, CA (US)

(73) Assignee: MASIMO CORPORATION, Irvine, CA (US)

( * ) Notice: Subject to any disclaimer, the term of this patent is extended or adjusted under 35 U.S.C. 154(b) by 422 days.

(21) Appl. No.: 14/743,479

(22) Filed: Jun. 18, 2015

(65) Prior Publication Data

US 2015/0366507 A1     Dec. 24, 2015

Related U.S. Application Data

(60) Provisional application No. 62/014,611, filed on Jun. 19, 2014.

(51) Int. Cl.
*A61B 5/00* (2006.01)
*A61B 5/1455* (2006.01)

(52) U.S. Cl.
CPC ........ *A61B 5/6844* (2013.01); *A61B 5/14552* (2013.01); *A61B 5/684* (2013.01); *A61B 5/6826* (2013.01); *A61B 2562/0257* (2013.01)

(58) Field of Classification Search
CPC . A61B 5/6826; A61B 5/6844; A61B 5/14552; A61B 2562/0257
See application file for complete search history.

(56) References Cited

U.S. PATENT DOCUMENTS

| | | |
|---|---|---|
| 4,960,128 A | 10/1990 | Gordon et al. |
| 4,964,408 A | 10/1990 | Hink et al. |
| 5,041,187 A | 8/1991 | Hink et al. |
| 5,069,213 A | 12/1991 | Polczynski |
| 5,163,438 A | 11/1992 | Gordon et al. |
| 5,319,355 A | 6/1994 | Russek |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| D361,840 S | 8/1995 | Savage et al. |
| D362,063 S | 9/1995 | Savage et al. |
| 5,452,717 A | 9/1995 | Branigan et al. |

(Continued)

*Primary Examiner* — Thaddeus B Cox

(74) *Attorney, Agent, or Firm* — Knobbe, Martens, Olson & Bear LLP

(57) ABSTRACT

Systems and methods are disclosed for proximity sensing in physiological sensors, and more specifically to using one or more proximity sensors located on or within a physiological sensor to determine the positioning of the physiological sensor on a patient measurement site. Accurate placement of a physiological sensor on the patient measurement site is a key factor in obtaining reliable measurement of physiological parameters of the patient. Proper alignment between a measurement site and a sensor optical assembly provides more accurate physiological measurement data. This alignment can be determined based on data from a proximity sensor or sensors placed on or within the physiological sensor.

18 Claims, 11 Drawing Sheets

(56) References Cited

U.S. PATENT DOCUMENTS

| | | |
|---|---|---|
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,534,851 A | 7/1996 | Russek |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,638,818 A | 6/1997 | Diab et al. |
| 5,638,816 A | 7/1997 | Kiani-Azarbayjany et al. |
| 5,645,440 A | 7/1997 | Tobler et al. |
| 5,685,299 A | 11/1997 | Diab et al. |
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,987,343 A | 11/1999 | Kinast |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,124,597 A | 9/2000 | Shehada |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,301,493 B1 | 10/2001 | Marro et al. |
| 6,308,089 B1 | 10/2001 | von der Ruhr et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kiani et al. |
| 6,661,161 B1 | 12/2003 | Lanzo et al. |
| 6,671,528 B2 * | 12/2003 | Steuer ............... A61B 5/14535 600/322 |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |

(56) References Cited

U.S. PATENT DOCUMENTS

| | | |
|---|---|---|
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,048,687 B1 | 5/2006 | Reuss et al. |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,596,398 B2 | 9/2009 | Al-Ali et al. |
| 7,618,375 B2 | 11/2009 | Flaherty |
| D606,659 S | 12/2009 | Kiani et al. |
| 7,647,083 B2 | 1/2010 | Al-Ali et al. |
| D609,193 S | 2/2010 | Al-Ali et al. |
| D614,305 S | 4/2010 | Al-Ali et al. |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Al-Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,533 B2 | 7/2012 | Diab et al. |

(56) References Cited

U.S. PATENT DOCUMENTS

| | | |
|---|---|---|
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,280,473 B2 | 10/2012 | Al-Ali |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellot et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,581,732 B2 | 11/2013 | Al-Ali et al. |
| 8,584,345 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 9,028,429 B2 | 5/2015 | Telfort et al. |
| 9,037,207 B2 | 5/2015 | Al-Ali et al. |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,078,560 B2 | 7/2015 | Schurman et al. |
| 9,084,569 B2 | 7/2015 | Weber et al. |
| 9,095,316 B2 | 8/2015 | Welch et al. |
| 9,106,038 B2 | 8/2015 | Telfort et al. |

(56) References Cited

U.S. PATENT DOCUMENTS

| | | |
|---|---|---|
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,176,141 B2 | 11/2015 | Al-Ali et al. |
| 9,186,102 B2 | 11/2015 | Bruinsma et al. |
| 9,192,312 B2 | 11/2015 | Al-Ali |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,072 B2 | 12/2015 | Kiani |
| 9,211,095 B1 | 12/2015 | Al-Ali |
| 9,218,454 B2 | 12/2015 | Kiani et al. |
| 9,226,696 B2 | 1/2016 | Kiani |
| 9,241,662 B2 | 1/2016 | Al-Ali et al. |
| 9,245,668 B1 | 1/2016 | Vo et al. |
| 9,259,185 B2 | 2/2016 | Abdul-Hafiz et al. |
| 9,267,572 B2 | 2/2016 | Barker et al. |
| 9,277,880 B2 | 3/2016 | Poeze et al. |
| 9,289,167 B2 | 3/2016 | Diab et al. |
| 9,295,421 B2 | 3/2016 | Kiani et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,333,316 B2 | 5/2016 | Kiani |
| 9,339,220 B2 | 5/2016 | Lamego et al. |
| 9,341,565 B2 | 5/2016 | Lamego et al. |
| 9,351,673 B2 | 5/2016 | Diab et al. |
| 9,351,675 B2 | 5/2016 | Al-Ali et al. |
| 9,364,181 B2 | 6/2016 | Kiani et al. |
| 9,368,671 B2 | 6/2016 | Wojtczuk et al. |
| 9,370,325 B2 | 6/2016 | Al-Ali et al. |
| 9,370,326 B2 | 6/2016 | McHale et al. |
| 9,370,335 B2 | 6/2016 | Al-ali et al. |
| 9,375,185 B2 | 6/2016 | Ali et al. |
| 9,386,953 B2 | 7/2016 | Al-Ali |
| 9,386,961 B2 | 7/2016 | Al-Ali et al. |
| 9,392,945 B2 | 7/2016 | Al-Ali et al. |
| 9,397,448 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,466,919 B2 | 10/2016 | Kiani et al. |
| 9,474,474 B2 | 10/2016 | Lamego et al. |
| 9,480,422 B2 | 11/2016 | Al-Ali |
| 9,480,435 B2 | 11/2016 | Olsen |
| 9,492,110 B2 | 11/2016 | Al-Ali et al. |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,538,949 B2 | 1/2017 | Al-Ali et al. |
| 9,538,980 B2 | 1/2017 | Telfort et al. |
| 9,549,696 B2 | 1/2017 | Lamego et al. |
| 9,554,737 B2 | 1/2017 | Schurman et al. |
| 9,560,996 B2 | 2/2017 | Kiani |
| 9,560,998 B2 | 2/2017 | Al-Ali et al. |
| 9,566,019 B2 | 2/2017 | Al-Ali et al. |
| 9,579,039 B2 | 2/2017 | Jansen et al. |
| 9,591,975 B2 | 3/2017 | Dalvi et al. |
| 9,622,692 B2 | 4/2017 | Lamego et al. |
| 9,622,693 B2 | 4/2017 | Diab |
| D788,312 S | 5/2017 | Al-Ali et al. |
| 9,636,055 B2 | 5/2017 | Al-Ali et al. |
| 9,636,056 B2 | 5/2017 | Al-Ali |
| 9,649,054 B2 | 5/2017 | Lamego et al. |
| 9,662,052 B2 | 5/2017 | Al-Ali et al. |
| 9,668,679 B2 | 6/2017 | Schurman et al. |
| 9,668,680 B2 | 6/2017 | Bruinsma et al. |
| 9,668,703 B2 | 6/2017 | Al-Ali |
| 9,675,286 B2 | 6/2017 | Diab |
| 9,687,160 B2 | 6/2017 | Kiani |
| 9,693,719 B2 | 7/2017 | Al-Ali et al. |
| 9,693,737 B2 | 7/2017 | Al-Ali |
| 9,697,928 B2 | 7/2017 | Al-Ali et al. |
| 9,717,425 B2 | 8/2017 | Kiani et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,730,640 B2 | 8/2017 | Diab et al. |
| 9,743,887 B2 | 8/2017 | Al-Ali et al. |
| 9,749,232 B2 | 8/2017 | Sampath et al. |
| 9,750,442 B2 | 9/2017 | Olsen |
| 9,750,443 B2 | 9/2017 | Smith et al. |
| 9,750,461 B1 | 9/2017 | Telfort |
| 9,775,545 B2 | 10/2017 | Al-Ali et al. |
| 9,775,546 B2 | 10/2017 | Diab et al. |
| 9,775,570 B2 | 10/2017 | Al-Ali |
| 9,778,079 B1 | 10/2017 | Al-Ali et al. |
| 9,782,077 B2 | 10/2017 | Lamego et al. |
| 9,782,110 B2 | 10/2017 | Kiani |
| 9,787,568 B2 | 10/2017 | Lamego et al. |
| 9,788,735 B2 | 10/2017 | Al-Ali |
| 9,788,768 B2 | 10/2017 | Al-Ali et al. |
| 9,795,300 B2 | 10/2017 | Al-Ali |
| 9,795,310 B2 | 10/2017 | Al-Ali |
| 9,795,358 B2 | 10/2017 | Telfort et al. |
| 9,795,739 B2 | 10/2017 | Al-Ali et al. |
| 9,801,556 B2 | 10/2017 | Kiani |
| 9,801,588 B2 | 10/2017 | Weber et al. |
| 9,808,188 B1 | 11/2017 | Perea et al. |
| 9,814,418 B2 | 11/2017 | Weber et al. |
| 9,820,691 B2 | 11/2017 | Kiani |
| 9,833,152 B2 | 12/2017 | Kiani et al. |
| 9,833,180 B2 | 12/2017 | Shakespeare et al. |
| 9,839,379 B2 | 12/2017 | Al-Ali et al. |
| 9,839,381 B1 | 12/2017 | Weber et al. |
| 9,847,002 B2 | 12/2017 | Kiani et al. |
| 9,847,749 B2 | 12/2017 | Kiani et al. |
| 9,848,800 B1 | 12/2017 | Lee et al. |
| 9,848,806 B2 | 12/2017 | Al-Ali et al. |
| 9,848,807 B2 | 12/2017 | Lamego |
| 9,861,298 B2 | 1/2018 | Eckerbom et al. |
| 9,861,304 B2 | 1/2018 | Al-Ali et al. |
| 9,861,305 B1 | 1/2018 | Weber et al. |
| 9,867,578 B2 | 1/2018 | Al-Ali et al. |
| 9,872,623 B2 | 1/2018 | Al-Ali |
| 9,876,320 B2 | 1/2018 | Coverston et al. |
| 9,877,650 B2 | 1/2018 | Muhsin et al. |
| 9,877,686 B2 | 1/2018 | Al-Ali et al. |
| 9,891,079 B2 | 2/2018 | Dalvi |
| 9,895,107 B2 | 2/2018 | Al-Ali et al. |
| 2005/0007125 A1 | 1/2005 | Heger |
| 2006/0161054 A1 | 7/2006 | Reuss et al. |
| 2007/0282478 A1 | 12/2007 | Al-Ali et al. |
| 2008/0033275 A1 | 2/2008 | Blank et al. |
| 2008/0319299 A1 | 12/2008 | Stippick et al. |
| 2009/0247984 A1 | 10/2009 | Lamego et al. |
| 2009/0275813 A1 | 11/2009 | Davis |
| 2009/0275844 A1 | 11/2009 | Al-Ali |
| 2010/0004518 A1 | 1/2010 | Vo et al. |
| 2010/0030040 A1 | 2/2010 | Poeze et al. |
| 2011/0082711 A1 | 4/2011 | Poeze et al. |
| 2011/0105854 A1 | 5/2011 | Kiani et al. |
| 2011/0125060 A1 | 5/2011 | Telfort et al. |
| 2011/0208015 A1 | 8/2011 | Welch et al. |
| 2011/0230733 A1 | 9/2011 | Al-Ali |
| 2012/0165629 A1 | 6/2012 | Merritt et al. |
| 2012/0209082 A1 | 8/2012 | Al-Ali |

(56) References Cited

U.S. PATENT DOCUMENTS

| | | |
|---|---|---|
| 2012/0209084 A1 | 8/2012 | Olsen et al. |
| 2012/0283524 A1 | 11/2012 | Kiani et al. |
| 2012/0319816 A1 | 12/2012 | Al-Ali |
| 2013/0023775 A1 | 1/2013 | Lamego et al. |
| 2013/0041591 A1 | 2/2013 | Lamego |
| 2013/0060147 A1 | 3/2013 | Welch et al. |
| 2013/0096405 A1 | 4/2013 | Garfio |
| 2013/0096936 A1 | 4/2013 | Sampath et al. |
| 2013/0243021 A1 | 9/2013 | Siskavich |
| 2013/0253334 A1 | 9/2013 | Al-Ali et al. |
| 2013/0296672 A1 | 11/2013 | O'Neil et al. |
| 2013/0296713 A1 | 11/2013 | Al-Ali et al. |
| 2013/0324808 A1 | 12/2013 | Al-Ali et al. |
| 2013/0331660 A1 | 12/2013 | Al-Ali et al. |
| 2014/0012100 A1 | 1/2014 | Al-Ali et al. |
| 2014/0051953 A1 | 2/2014 | Lamego et al. |
| 2014/0081175 A1 | 3/2014 | Telfort |
| 2014/0120564 A1 | 5/2014 | Workman et al. |
| 2014/0121482 A1 | 5/2014 | Merritt et al. |
| 2014/0127137 A1 | 5/2014 | Bellott et al. |
| 2014/0135588 A1 | 5/2014 | Al-Ali et al. |
| 2014/0135602 A1 * | 5/2014 | Lemke ............... A61B 5/6829 600/324 |
| 2014/0163344 A1 | 6/2014 | Al-Ali |
| 2014/0163402 A1 | 6/2014 | Lamego et al. |
| 2014/0166076 A1 | 6/2014 | Kiani et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0180160 A1 | 6/2014 | Brown et al. |
| 2014/0187973 A1 | 7/2014 | Brown et al. |
| 2014/0213864 A1 | 7/2014 | Abdul-Hafiz et al. |
| 2014/0266790 A1 | 9/2014 | Al-Ali et al. |
| 2014/0275808 A1 | 9/2014 | Poeze et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0276115 A1 | 9/2014 | Dalvi et al. |
| 2014/0288400 A1 | 9/2014 | Diab et al. |
| 2014/0316217 A1 | 10/2014 | Purdon et al. |
| 2014/0316218 A1 | 10/2014 | Purdon et al. |
| 2014/0316228 A1 | 10/2014 | Blank et al. |
| 2014/0323825 A1 | 10/2014 | Al-Ali et al. |
| 2014/0323897 A1 | 10/2014 | Brown et al. |
| 2014/0323898 A1 | 10/2014 | Purdon et al. |
| 2014/0330092 A1 | 11/2014 | Al-Ali et al. |
| 2014/0330098 A1 | 11/2014 | Merritt et al. |
| 2014/0357966 A1 | 12/2014 | Al-Ali et al. |
| 2015/0005600 A1 | 1/2015 | Blank et al. |
| 2015/0011907 A1 | 1/2015 | Purdon et al. |
| 2015/0012231 A1 | 1/2015 | Poeze et al. |
| 2015/0032029 A1 | 1/2015 | Al-Ali et al. |
| 2015/0038859 A1 | 2/2015 | Dalvi et al. |
| 2015/0080754 A1 | 3/2015 | Purdon et al. |
| 2015/0087936 A1 | 3/2015 | Al-Ali et al. |
| 2015/0094546 A1 | 4/2015 | Al-Ali |
| 2015/0097701 A1 | 4/2015 | Al-Ali et al. |
| 2015/0099950 A1 | 4/2015 | Al-Ali et al. |
| 2015/0099955 A1 | 4/2015 | Al-Ali et al. |
| 2015/0101844 A1 | 4/2015 | Al-Ali et al. |
| 2015/0106121 A1 | 4/2015 | Muhsin et al. |
| 2015/0112151 A1 | 4/2015 | Muhsin et al. |
| 2015/0116076 A1 | 4/2015 | Al-Ali et al. |
| 2015/0126830 A1 | 5/2015 | Schurman et al. |
| 2015/0165312 A1 | 6/2015 | Kiani |
| 2015/0196249 A1 | 7/2015 | Brown et al. |
| 2015/0216459 A1 | 8/2015 | Al-Ali et al. |
| 2015/0238722 A1 | 8/2015 | Al-Ali |
| 2015/0245773 A1 | 9/2015 | Lamego et al. |
| 2015/0245794 A1 | 9/2015 | Al-Ali |
| 2015/0257689 A1 | 9/2015 | Al-Ali et al. |
| 2015/0272514 A1 | 10/2015 | Kiani et al. |
| 2015/0351697 A1 | 12/2015 | Weber et al. |
| 2015/0359429 A1 | 12/2015 | Al-Ali et al. |
| 2016/0029932 A1 | 2/2016 | Al-Ali |
| 2016/0058347 A1 | 3/2016 | Reichgott et al. |
| 2016/0066824 A1 | 3/2016 | Al-Ali et al. |
| 2016/0081552 A1 | 3/2016 | Wojtczuk et al. |
| 2016/0095543 A1 | 4/2016 | Telfort et al. |
| 2016/0095548 A1 | 4/2016 | Al-Ali et al. |
| 2016/0103598 A1 | 4/2016 | Al-Ali et al. |
| 2016/0143548 A1 | 5/2016 | Al-Ali |
| 2016/0166182 A1 | 6/2016 | Al-Ali et al. |
| 2016/0166183 A1 | 6/2016 | Poeze et al. |
| 2016/0192869 A1 | 7/2016 | Kiani et al. |
| 2016/0196388 A1 | 7/2016 | Lamego |
| 2016/0197436 A1 | 7/2016 | Barker et al. |
| 2016/0213281 A1 | 7/2016 | Eckerbom et al. |
| 2016/0228043 A1 | 8/2016 | O'Neil et al. |
| 2016/0233632 A1 | 8/2016 | Scruggs et al. |
| 2016/0234944 A1 | 8/2016 | Schmidt et al. |
| 2016/0270735 A1 | 9/2016 | Diab et al. |
| 2016/0283665 A1 | 9/2016 | Sampath et al. |
| 2016/0287090 A1 | 10/2016 | Al-Ali et al. |
| 2016/0287786 A1 | 10/2016 | Kiani |
| 2016/0296169 A1 | 10/2016 | McHale et al. |
| 2016/0310052 A1 | 10/2016 | Al-Ali et al. |
| 2016/0314260 A1 | 10/2016 | Kiani |
| 2016/0324486 A1 | 11/2016 | Al-Ali et al. |
| 2016/0324488 A1 | 11/2016 | Olsen |
| 2016/0327984 A1 | 11/2016 | Al-Ali et al. |
| 2016/0328528 A1 | 11/2016 | Al-Ali et al. |
| 2016/0331332 A1 | 11/2016 | Al-Ali |
| 2016/0367173 A1 | 12/2016 | Dalvi et al. |
| 2017/0000394 A1 | 1/2017 | Al-Ali et al. |
| 2017/0007134 A1 | 1/2017 | Al-Ali et al. |
| 2017/0007198 A1 | 1/2017 | Al-Ali et al. |
| 2017/0014083 A1 | 1/2017 | Diab et al. |
| 2017/0014084 A1 | 1/2017 | Al-Ali et al. |
| 2017/0027456 A1 | 2/2017 | Kinast et al. |
| 2017/0042488 A1 | 2/2017 | Muhsin |
| 2017/0055851 A1 | 3/2017 | Al-Ali |
| 2017/0055882 A1 | 3/2017 | Al-Ali et al. |
| 2017/0055887 A1 | 3/2017 | Al-Ali |
| 2017/0055896 A1 | 3/2017 | Al-Ali et al. |
| 2017/0079594 A1 | 3/2017 | Telfort et al. |
| 2017/0086723 A1 | 3/2017 | Al-Ali et al. |
| 2017/0143281 A1 | 5/2017 | Olsen |
| 2017/0147774 A1 | 5/2017 | Kiani |
| 2017/0156620 A1 | 6/2017 | Al-Ali et al. |
| 2017/0173632 A1 | 6/2017 | Al-Ali |
| 2017/0187146 A1 | 6/2017 | Kiani et al. |
| 2017/0188919 A1 | 7/2017 | Al-Ali et al. |
| 2017/0196464 A1 | 7/2017 | Jansen et al. |
| 2017/0196470 A1 | 7/2017 | Lamego et al. |
| 2017/0202490 A1 | 7/2017 | Al-Ali et al. |
| 2017/0224262 A1 | 8/2017 | Al-Ali |
| 2017/0228516 A1 | 8/2017 | Sampath et al. |
| 2017/0245790 A1 | 8/2017 | Al-Ali et al. |
| 2017/0251974 A1 | 9/2017 | Shreim et al. |
| 2017/0251975 A1 | 9/2017 | Shreim et al. |
| 2017/0258403 A1 | 9/2017 | Abdul-Hafiz et al. |
| 2017/0311891 A1 | 11/2017 | Kiani et al. |
| 2017/0325728 A1 | 11/2017 | Al-Ali et al. |
| 2017/0332976 A1 | 11/2017 | Al-Ali et al. |
| 2017/0340293 A1 | 11/2017 | Al-Ali et al. |
| 2017/0360310 A1 | 12/2017 | Kiani et al. |
| 2017/0367632 A1 | 12/2017 | Al-Ali et al. |
| 2018/0008146 A1 | 1/2018 | Al-Ali et al. |
| 2018/0014752 A1 | 1/2018 | Al-Ali et al. |
| 2018/0028124 A1 | 2/2018 | Al-Ali et al. |

\* cited by examiner

PROXIMITY SENSOR IN PULSE OXIMETER

CROSS-REFERENCE TO RELATED APPLICATIONS

This application claims the benefit of U.S. Provisional Application Ser. No. 62/014,611, filed Jun. 19, 2014, titled "PROXIMITY SENSOR IN PULSE OXIMETER," the entirety of which is hereby incorporated by reference.

TECHNICAL FIELD

The systems and methods disclosed herein are directed to patient monitoring, and, more particularly, to pulse oximeter patient monitors capable of capacitive proximity detection.

BACKGROUND

The standard of care in caregiver environments includes patient monitoring through spectroscopic analysis using, for example, a pulse oximeter. Devices capable of spectroscopic analysis generally include a light source(s) transmitting optical radiation into or reflecting off a measurement site, such as, body tissue carrying pulsing blood. After attenuation by tissue and fluids of the measurement site, a photo-detection device(s) detects the attenuated light and outputs a detector signal(s) responsive to the detected attenuated light. A signal processing device(s) process the detector(s) signal(s) and outputs a measurement indicative of a blood constituent of interest, such as glucose, oxygen, methemoglobin, total hemoglobin, other physiological parameters, or other data or combinations of data useful in determining a state or trend of wellness of a patient.

In noninvasive devices and methods, a sensor is often adapted to position a finger proximate the light source and light detector. For example, noninvasive finger clip sensors often include a clothespin-shaped housing that includes a contoured bed conforming generally to the shape of a finger.

Accurate determination of physiological measurements is often dependent upon proper application of the optical sensor to the measurement site. Clip-type pulse oximeter sensors typically include a physical stop near the hinge of the housing to indicate desired placement of a user's finger or other measurement site within the sensor. However, the physical stop does not ensure that the patient's finger is positioned far enough into the sensor. In addition, even if a sensor is initially placed correctly, movement, either of the patient or of the sensor during artificial pulsing, can longitudinally displace the patient's finger within the sensor. This can result in the light source and detector of the oximeter being positioned around a portion of the finger that provides inaccurate physiological measurements.

SUMMARY

The foregoing and other problems are addressed, in some embodiments, by providing an oximeter with proximity sensing technology that can be used to determine whether the oximeter is correctly applied to a patient measurement site. For example, one or more capacitive sensor electrodes can provide an indication to a processor of the oximeter regarding whether the sensor is correctly positioned by sensing proximity to the skin of the measurement site. Capacitive sensor electrodes can provide data representing a distance or relative distance between the electrodes and skin of the measurement site. Due to the inverse relationship between capacitance and distance, the sensitivity to the distance between the measurement site and the capacitive sensor electrodes increases as the distance between the measurement site and the capacitive sensor electrodes decreases. Accordingly, in one embodiment, a plurality of capacitive sensor electrodes can be positioned at various locations within the oximeter housing to provide proximity accurate feedback when the measurement site is located at a number of different positions relative to the oximeter. Though discussed primarily herein in the context of capacitive sensor electrodes, proximity feedback in pulse oximeters can be provided in other examples by optical, mechanical, or electrical sensors interfacing with skin of a measurement site, or a combination of one or more of capacitive, optical, mechanical, and electrical sensors.

In some embodiments, capacitive sensor electrodes can be used to determine the longitudinal displacement of a patient's finger within a clip-type pulse oximeter sensor housing. Using the determined displacement, the oximeter can determine whether to provide an indication to the patient or physician to reposition the oximeter. The oximeter can additionally or alternatively use the determined displacement to determine whether to mechanically reposition the optical assembly of the oximeter relative to the patient's finger. In oximeters implementing artificial pulsing, the capacitive sensor electrodes can periodically or continuously monitor the longitudinal displacement of the patient's finger within the sensor housing to determine a probe off condition. These examples illustrate some of the many benefits of an oximeter sensor having proximity sensing technology for determining positioning of the sensor relative to a measurement site.

For purposes of summarizing the disclosure, certain aspects, advantages and novel features of the inventions have been described herein. It is to be understood that not necessarily all such advantages can be achieved in accordance with any particular embodiment of the inventions disclosed herein. Thus, the inventions disclosed herein can be embodied or carried out in a manner that achieves or optimizes one advantage or group of advantages as taught herein without necessarily achieving other advantages as can be taught or suggested herein.

BRIEF DESCRIPTION OF THE DRAWINGS

Throughout the drawings, reference numbers can be re-used to indicate correspondence between referenced elements. The drawings are provided to illustrate embodiments of the inventions described herein and not to limit the scope thereof.

DETAILED DESCRIPTION

I. Introduction

Implementations described herein relate generally to proximity sensing in physiological sensors, and more specifically to using one or more proximity sensors located on or within a physiological sensor to determine the positioning of the physiological sensor on a patient measurement site. Accurate placement of a physiological sensor on the patient measurement site is a key factor in obtaining reliable measurement of physiological parameters of the patient. For example, in clip-type pulse oximeter sensors, longitudinal positioning of the patient's finger within the sensor housing determines which portion of the patient's finger is aligned with an optical assembly used to generate physiological measurement data for determining one or more physiological parameters. Proper alignment with the optical assembly covers a detector of the optical assembly with the patient's fingertip and reduces introduction of ambient light to the detector, and accordingly provides more accurate physiological measurement data. This alignment can be determined based on data from a proximity sensor or sensors placed on or within the physiological sensor. Suitable proximity sensors include one or more capacitive sensors, optical scanning sensors, electrical sensors, or mechanical contact sensors.

The proximity data generated by the proximity sensors on or within a pulse oximeter can enable provision of more accurate physiological measurement data. For example, the proximity sensors described herein can be used to provide an indication to the oximeter to generate feedback for a patient or physician to reposition an improperly aligned oximeter sensor. In another example, the proximity sensors can be used to provide alignment information for mechanically repositioning the optical assembly with respect to the oximeter housing and patient finger. As a further example, the proximity sensors can be used to determine a probe off condition indicating that physiological measurement data obtained during persistence of the probe off condition should be discarded due to improper alignment. In additional examples, the proximity sensors can be used to associate distance data with measurement data output by the sensor, e.g. for assigning a confidence value to the measurement data.

II. Overview of Example Proximity Sensing Physiological Monitoring Systems

Figure 1A:
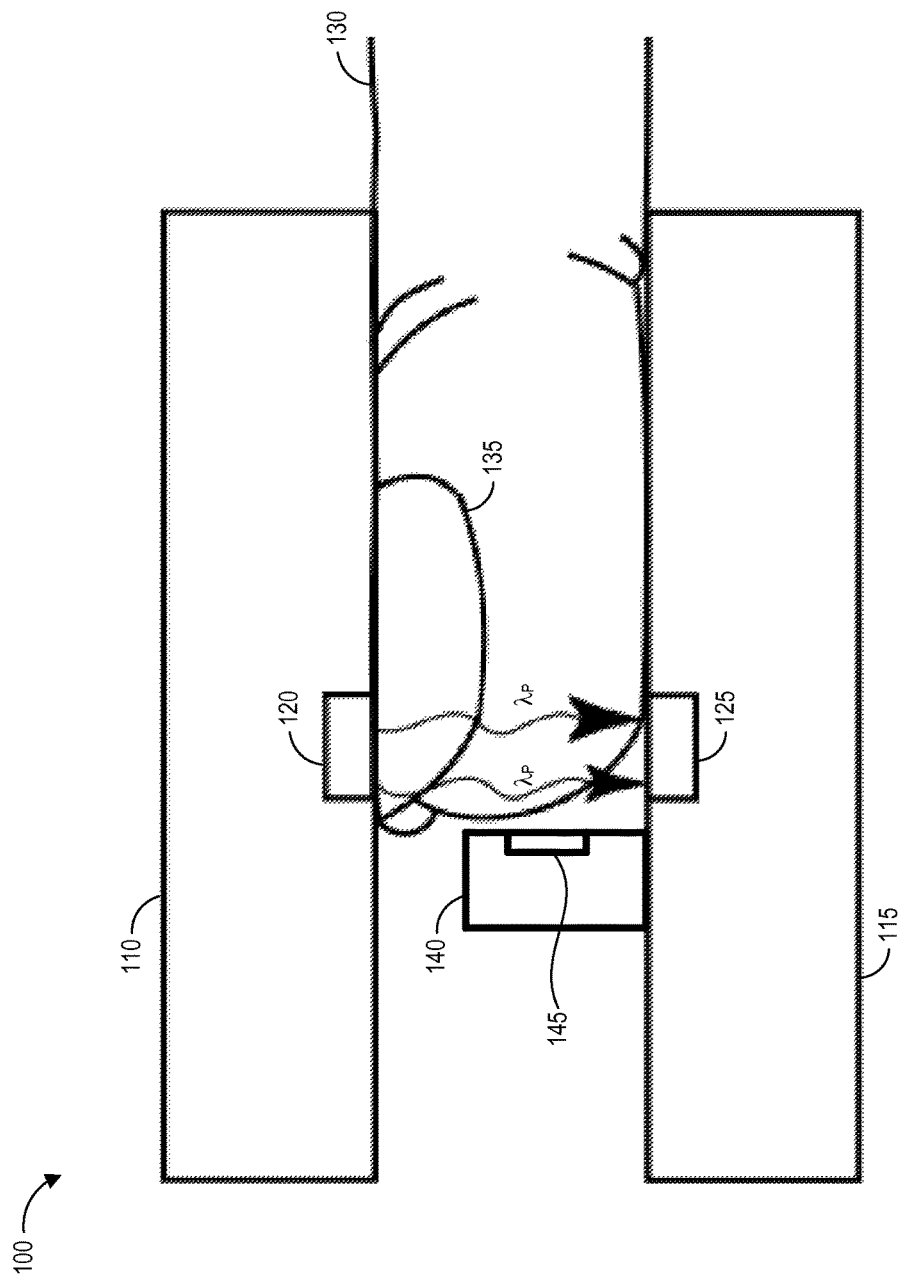
FIG. 1A illustrates a high-level diagram of an embodiment of a physiological sensor having proximity sensing capabilities positioned around a patient measurement site.
Figure 1B:
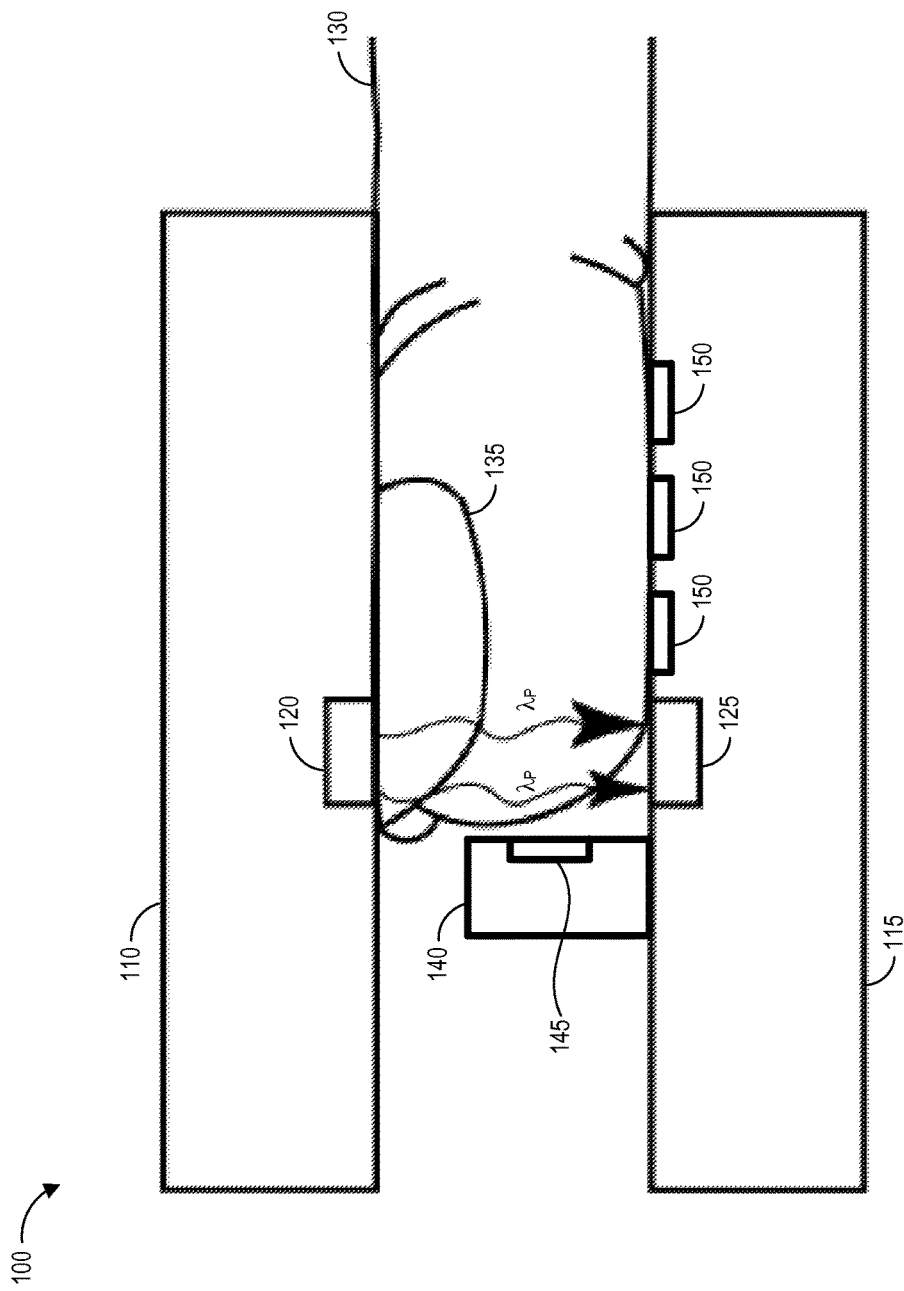
FIG. 1B illustrates another embodiment of the physiological sensor of FIG. 1A.

FIGS. 1A and 1B illustrate embodiments of a high-level diagram of an embodiment of a physiological sensor having proximity sensing capabilities positioned around a patient measurement site. The sensor 100 can include a first housing component 110 including an emitter 120 and a second housing component 115 including a detector 125. The sensor 100 can also include a physical stop 140 to guide the positioning of a patient finger 130 or other measurement site within the sensor 100. One or more proximity sensors 145 can be positioned on or within the sensor 100.

The emitter 120 can be configured to emit light having multiple primary wavelengths $\lambda_P$ into the tissue of the patient finger 130 or other measurement site. The emitter 120 can be comprised of one or more devices such as semi-conductive light emitting diodes (LEDs), although it will be appreciated that other light generating devices may be used. The light emitter 120 may be chosen to emit light at a single known discrete wavelength, at multiple discrete wavelengths, or across a portion of the spectrum (such as that emitted by a "white light" LED), depending on the needs of the particular application. In one embodiment, the emitter 120 consists of two or more diodes emitting light energy in the infrared and red regions of the electromagnetic spectrum, and a parallel resistor (or resistors) used for security. The construction and operation of such light source drive circuitry is described in U.S. Pat. No. 5,758,644 incorporated herein by reference.

The detector 125 can be any suitable light energy detector responsive to light energy from the emitter, for example a semi-conductive photodetector. The emitter 120 and detector 125 can be aligned such that the detector 125 detects the emitted light after attenuation by the tissue of the patient finger 130.

The physical stop 140 can provide tactile feedback to a clinician or patient positioning the finger 130 within the sensor in order to achieve proper positioning. Proper positioning of the patient finger 130 or other tissue site relative to the detector 125 enables accurate physiological measurements to be made. In particular, the emitter 120 is placed so as to illuminate a blood-perfused tissue site 135, such as a nail bed, and the detector 125 is positioned so that only light transmitted by the emitter 120 and attenuated by pulsatile blood flowing within the tissue site 135 is received by the detector 125.

Physical stop 140 can prevent the tissue site 135 from being positioned beyond the emitter 120 and detector 125, that is, too far into the sensor 100. However, the physical stop 140 does not ensure that the tissue site 135 will be placed far enough within the sensor 100 for adequate transmission of light from the emitter 120 through the tissue site 135 to the detector 125 to enable clinically accurate physiological measurements. Accordingly, the sensor 100 can be provided with one or more proximity sensors 145 positioned within the sensor housing. The proximity sensor(s) 145 can be used to determine whether the tissue site 135 is positioned properly relative to the emitter 120 and detector 125.

Proximity sensor 145 can be a capacitive sensor, in some embodiments, that uses capacitance of the human body as an input to determine a distance between the patient's finger 130 and the proximity sensor 145. In another embodiment, proximity sensor 145 can be an optical scanning sensor, for example a camera or a near-infrared proximity sensor that uses light to determine how close or far the patient's finger 130 is from the proximity sensor 145. In still further embodiments, proximity sensor 145 can be a mechanical contact sensor that determines whether physical contact is made between the patient's finger 130 and the proximity sensor 145 mounted on the physical stop 140. Other sensors suitable for determining contact or distance between patient finger 130 and sensor 145 can be used in other embodiments.

As illustrated by FIG. 1A, the physical stop 140 can include a proximity sensor 145. The proximity sensor 145 of FIG. 1A can be used to determine the distance (or whether there is contact) between the location of the proximity sensor 145 on the physical stop 140 and the end of the patient's finger 130 nearest the stop 140. The proximity sensor 145 can be positioned on the physical stop 140 so as to sense or contact a portion of the patient fingertip below the nail, in particular for embodiments in which a capacitive proximity sensor is implemented. As illustrated by FIG. 1B, an additional array of proximity sensors 145 can be positioned longitudinally along the finger bed of the second housing component 115. The array 150 of proximity sensors can provide additional feedback regarding the longitudinal positioning of the patient finger 130 within the sensor 100.

Figure 2A:
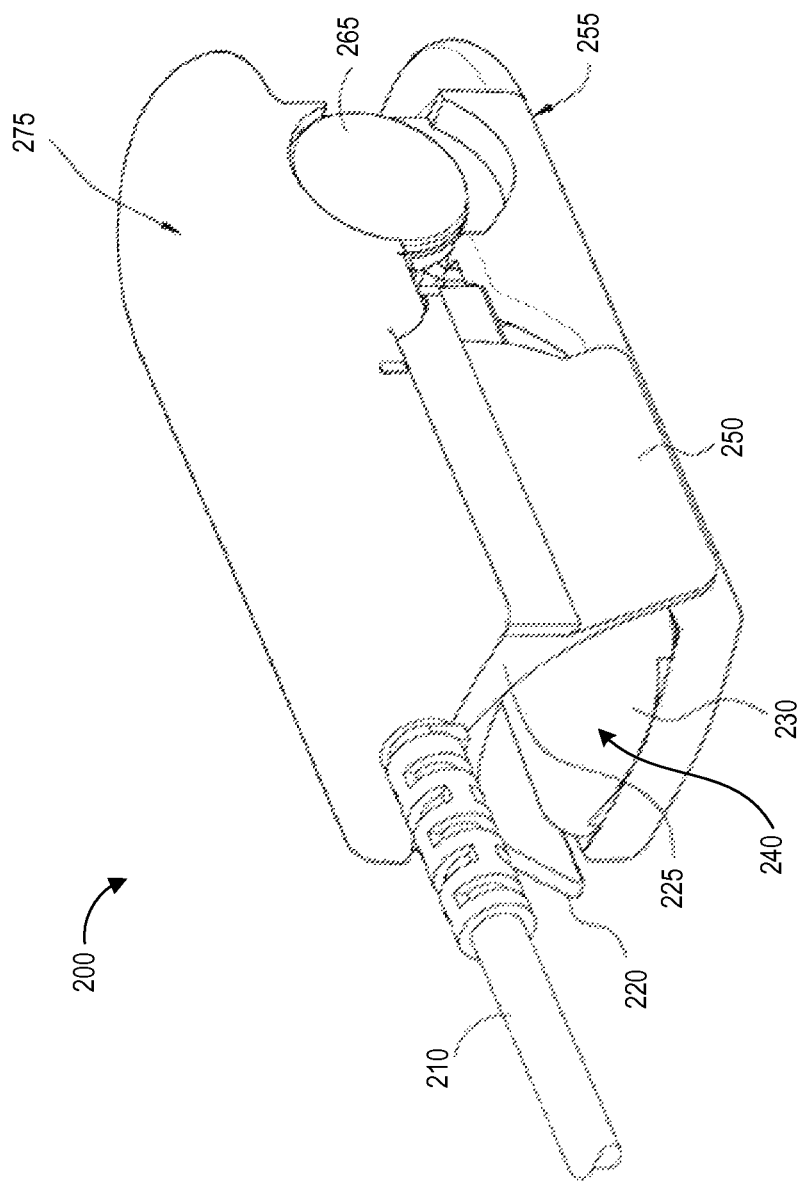
FIG. 2A illustrates a perspective view of an embodiment of a physiological sensor having proximity sensing capabilities.
Figure 2B:
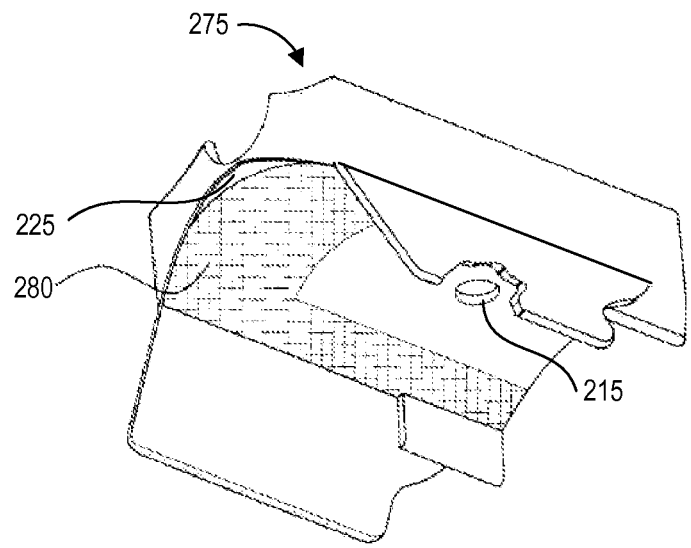
FIGS. 2B and 2C illustrate an exploded view of two components of the physiological sensor of FIG. 2A when disassembled.

As illustrated in FIGS. 2A and 2B, an embodiment of a sensor 200 can include a two-piece housing and an electrical supply and signal cable 210. The housing consists of a first (upper) housing element 275 and a second (lower) housing element 255, which can be rotatably attached to one another via a pivot element 265. A light emitter can be disposed within the upper housing element 275, while a detector can be disposed within the lower housing element 255. The housing is adapted to receive the distal end of a finger as shown in the block diagrams of FIGS. 1A and 1B, with the "upper" housing element 275 engaging the upper surface of the finger, and the "lower" housing element engaging the lower surface of the finger. It will be recognized, however, that the sensor 200 may be used in any orientation, such as with the first housing element 275 being located below the second housing element 255. Furthermore, the light emitter may alternatively be placed in the lower housing element 255, and the detector in the upper housing element 275 if desired, subject to modification of other probe components as described further below. It is also noted that while the following discussion describes a series of exemplary embodiments based on measuring the optical characteristics of a finger, the sensor 200 may be adapted for use with any number of other body parts, such as earlobes or loose skin, with equal success. Additional details of an embodiment of the sensor are disclosed in U.S. Pat. No. 6,580,086 entitled "Shield Optical Probe and Method," filed on Oct. 19, 1999 and assigned to Masimo Corporation, the entirety of which is hereby incorporated by reference.

The first and second housing elements 275, 255 can be generally rectangular in form with a pivot element 265 disposed near a common end of each of the elongate housing elements 275, 255. The two housing elements 275, 255 can be biased around the rotational axis of the pivot element by a biasing element, for example a hinge spring. The upper housing element 275 can be accordingly biased against the lower housing element 255 for secure placement on a patient finger or other measurement site. The user can grasp the sensor 200 between his or her fingers and separate the probe housing elements 275, 255 by applying force counter to the spring biasing force. In this fashion, the user simply grasps the sensor 200, opens it by applying a light force with the grasping fingers, and inserts the distal end of the patient's finger into the end 240 of the sensor 200. Once the finger is inserted into the sensor 200, the disproportionate compression of the finger (due to interaction of the angled housing elements 275, 255 and the substantially cylindrical finger) and the aforementioned bias spring separating force act to lower housing elements 275, 255 substantially parallel to each other, allowing more of the surface area of the upper and lower support surface elements 225, 230 to contact the finger, and for more even pressure distribution thereon. This assists with accurate positioning of the finger with respect to the emitter and detector for clinically accurate physiological measurement readings using the sensor 200.

Figure 2C:
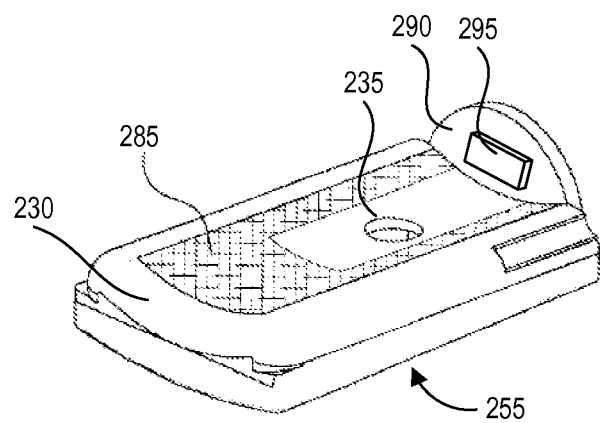

As shown in more detail in FIGS. 2B and 2C, the housing elements 275, 255 can include first (upper) and second (lower) support surface elements 225, 230, respectively, which provide support and alignment for the tissue material, such as the finger, when the sensor 200 is clamped thereon. The upper support surface element 225 can be fashioned from a substantially pliable polymer such as silicone rubber, so as to permit some deformation of the element 225 when in contact with the fairly rigid upper portion 280 of the patient's finger. The upper support surface element 225 further includes an optical energy shield 250 which protrudes from the upper support surface element 225. The shield 250 can be sized and shaped so as to conform substantially to the outer circumference of the patient's finger, providing at least a partial seal against ambient light incident on the probe exterior and otherwise exposed portions of the finger. In this fashion, patients having fingers of different circumferences can be accommodated with the same sensor 200 due to use of shield 250. The lower surface element 230 can be fashioned from a substantially solid and rigid (i.e., higher durometer) polymer. This harder, solid polymer can be used for the lower surface element 230 since the lower portion of the finger is generally more fleshy and deformable, thereby allowing the skin and tissue material thereof to deform and contour to the shape of the inner region 285 of the lower surface element. The inner regions 280, 285 can be contoured to assist in mitigating the effects of patient movement during operation of the sensor 200. Accordingly, the construction of the sensor 200 provides some alignment between the patient finger and the sensor 200 for proper positioning relative to the emitter and detector.

The upper surface element 225 includes an aperture 215 for transmission of light therethrough after emission by the emitter in the upper housing element 275. The lower surface element 230 includes an aperture 235 aligned with the detector for transmission of light therethrough after passing through the measurement site. The apertures 215, 235 allow for light energy to be transmitted between the light emitter and tissue material of the measurement site, and similarly between the tissue material and detector. The first aperture 215 is also axially located with the second aperture 235 in the vertical dimension, such that when the probe 100 is in the closed configuration with the patient's finger disposed between the upper and lower surface support elements 225, 230, light emitted by the light source through the first aperture 215 is transmitted through the finger and the second aperture 235 and received by the detector. Hence, the light source, first aperture 215, second aperture 235, and detector are substantially axial in this configuration.

The lower support element 230 is further provided with a physical stop 290 disposed near the pivot element of the sensor 200. The physical stop 290 is oriented vertically with respect to the lower support element 230 so as to stop the distal end of the patient's finger from being inserted into the probe past a certain point, thereby facilitating proper alignment of the finger within the sensor 200, especially with respect to the source and detector apertures 215, 235. While the present embodiment uses a semi-circular tab as the physical stop 290, it will be recognized that other configurations and locations of the physical stop 290 may be used. For example, the tab could be bifurcated with a portion being located on the upper support surface element 230, and a portion on the lower support surface element 225. Alternatively, the positioning element could be in the form of a tapered collar which receives, aligns, and restrains only the distal portion of the patient's finger. Many such alternative embodiments of the positioning element are possible, and considered to be within the scope of the present invention.

A proximity sensor 295 is positioned on the physical stop 290 that can be used to determine whether the patient finger or other measurement site is positioned properly within the sensor 200. As discussed above, proximity sensor 295 can be a capacitive sensor, an optical scanning sensor, or a mechanical contact sensor, or a combination of two or more of these sensors in some embodiments. Proximity sensor 295 provides feedback regarding distance or contact between the patient finger and the proximity sensor 295 located on physical stop 290, and accordingly can be used to determine whether the patient finger is aligned with the emitter and detector of the sensor 200. This feedback can be used to provide a repositioning indication to the user of the sensor 200, to mechanically reposition the optical components of the sensor 200, or for data filtering, as described in more detail below. Accordingly, the feedback from the proximity sensor 295 can enable more accurate physiological measurements using the sensor 200.

Figure 3A:
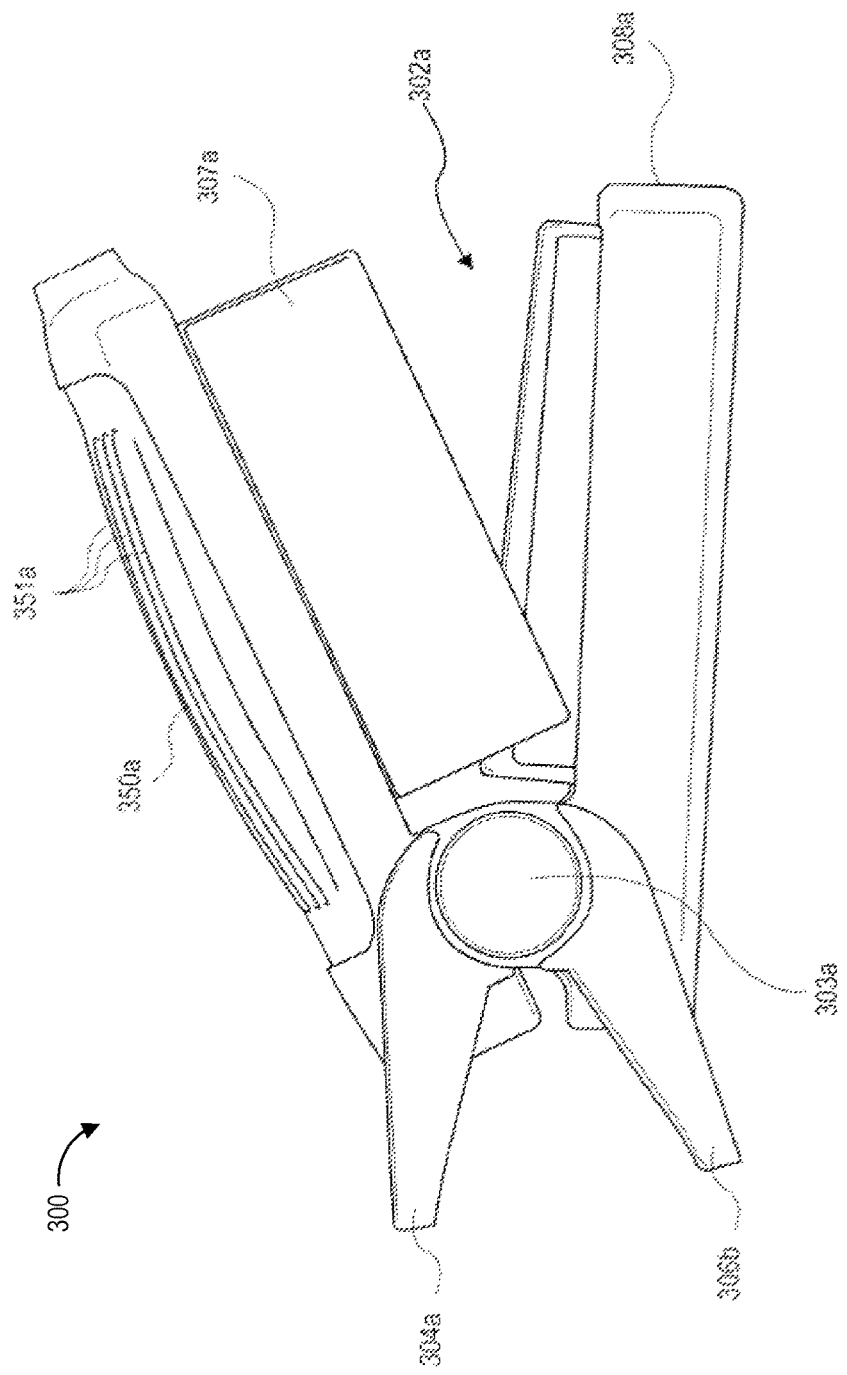
FIG. 3A illustrates a perspective view of another embodiment of a physiological sensor having proximity sensing capabilities.
Figure 3B:
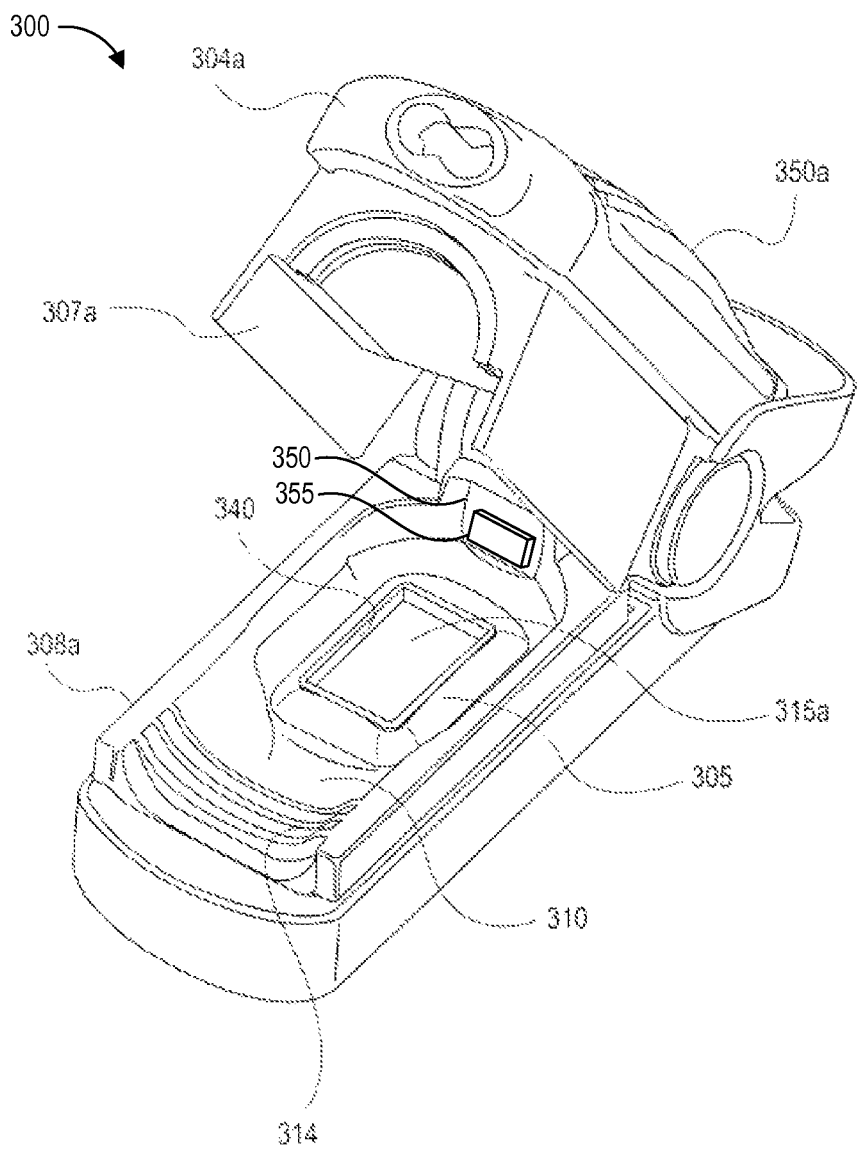
FIG. 3B illustrates a perspective view of the physiological sensor of FIG. 3A in an open position.

FIGS. 3A and 3B illustrate another embodiment of a sensor 300. The sensor 300 shown can include all of the features of the sensors 100 and 200 described above.

Referring to FIG. 3A, the sensor 300 in the depicted embodiment is a clothespin-shaped clip sensor that includes an enclosure 302a for receiving a patient's finger. The enclosure 302a is formed by an upper housing or emitter shell 304a, which is pivotably connected with a lower housing or detector shell 306a. The emitter shell 304a can be biased with the detector shell 306a to close together around a pivot point 303a and thereby sandwich finger tissue between the emitter and detector shells 304a, 306a.

In an embodiment, the pivot point 303a advantageously includes a pivot capable of adjusting the relationship between the emitter and detector housings 304a, 306a to effectively level the sections when applied to a tissue site. In another embodiment, the sensor 300 includes some or all features of the finger clip described in U.S. Pat. No. 8,437,825, entitled "Contoured Protrusion for Improving Spectroscopic Measurement of Blood Constituents," filed on Jul. 2, 2009 and assigned to Cercacor Laboratories, the entirety of which is hereby incorporated by reference. For example, the sensor 300 can include a spring that causes finger clip forces to be distributed along the finger.

The emitter housing 304a can position and house various emitter components of the sensor 301a. It can be constructed of reflective material (e.g., white silicone or plastic) and/or can be metallic or include metalicized plastic (e.g., including carbon and aluminum) to possibly serve as a heat sink including one or more fins 351a. The emitter housing 304a can also include absorbing opaque material, such as, for example, black or grey colored material, at various areas, such as on one or more flaps 307a, to reduce ambient light entering the sensor 301a. The emitter housing 304a can also include optical shield 307a to block ambient light from entering the sensor 300.

The detector housing 306a can position and house one or more detector portions of the sensor 301a. The detector housing 306a can be constructed of reflective material, such as white silicone or plastic. As noted, such materials can increase the usable signal at a detector by forcing light back into the tissue and measurement site (see FIG. 1). The detector housing 306a can also include absorbing opaque material at various areas, such as lower area 308a, to reduce ambient light entering the sensor 301a.

Referring to FIG. 3B, an example of finger bed 310 is shown in the sensor 301b. The finger bed 310 includes a generally curved surface shaped generally to receive tissue, such as a human digit. The finger bed 310 includes one or more ridges or channels 314. Each of the ridges 314 has a generally convex shape that can facilitate increasing traction or gripping of the patient's finger to the finger bed. Advantageously, the ridges 314 can improve the accuracy of spectroscopic analysis in certain embodiments by reducing noise that can result from a measurement site moving or shaking loose inside of the sensor 301a. The ridges 314 can be made from reflective or opaque materials in some embodiments to further increase signal to noise ration (SNR). In other implementations, other surface shapes can be used, such as, for example, generally flat, concave, or convex finger beds 310.

Finger bed 310 can also include an embodiment of a tissue thickness adjuster or protrusion 305. The protrusion 305 includes a measurement site contact area 370 that can contact body tissue of a measurement site. The protrusion 305 can be removed from or integrated with the finger bed 310. Interchangeable, different shaped protrusions 305 can also be provided, which can correspond to different finger shapes, characteristics, opacity, sizes, or the like. In some embodiments, protrusion 305 can include one or more proximity sensors to determine positioning of a patient finger over the protrusion 305.

The detector housing 306a can also include a physical stop 350 to prevent a patient's finger from being longitudinally placed too far into the sensor for proper alignment with the emitter and detector. Proper positioning of the patient finger or other tissue site relative to the detector enables accurate physiological measurements to be made. The physical stop 350 can include one or more proximity sensors 355 for determining distance or contact between the end of the patient's finger and the proximity sensor 355 to provide feedback regarding alignment of the patient's finger with the emitter and detector. As described above, the proximity sensor 355 can be a capacitive sensor, optical scanning sensor, or mechanical contact sensor. Data from proximity sensor 355 can be used to determine whether the patient finger is aligned with the emitter and detector of the sensor 300. This feedback can be used to provide a repositioning indication to the user of the sensor 300, to mechanically reposition the optical components of the sensor 200, or for data filtering, as described in more detail below. Accordingly, the feedback from the proximity sensor 295 can enable more accurate physiological measurements using the sensor 200.

In a vascular bed the arterial vasculature is coupled mechanically to the venous vasculature through the tissues. Although this coupling is small, the optical arterial pulse, e.g. photo-plethysmograph, has invariably a small venous component. This component is not fixed across subjects but its average is indirectly calibrated for in the saturation calibration curve. Its effect on the arterial pulse is proportional to the coupling size as well as the difference between the arterial and venous saturations at the site. Its effects may be explained by the reduction in the optical effect of venous coupling as the delta saturation between the arterial and the venous is reduced due to the increase in availability of plasma oxygen. Under this condition, the venous blood will look, optically, a lot like the arterial blood. Hence, the size of the Red photo-plethysmograph signal will shrink with respect to the IR indicating a shrinking $\Delta$Sat, i.e. higher venous saturation. In 1995, Masimo Corporation (Masimo) introduced a new technique for calculation the venous oxygen saturation (SpvO$_2$) by introducing an artificial pulse into the digit (see, e.g., U.S. Pat. No. 5,638,816, incorporated herein by reference).

The sensor 300 depicted in FIGS. 3A and 3B can be capable of introducing an artificial pulse into the measurement site. The sensor 300 can induce an artificial pulse at a frequency distinguishable from the frequency of a human arterial pulse. As a result, information related to both the arterial pulse as well as the artificial pulse is recoverable from the body. The redundant nature of both pieces of information provide additional information useful in determining physiological parameters.

Introducing an artificial excitation can cause perturbations in the blood flow similar to the effects of a heart beat. These artificial excitations can be used as an alternative to the natural pulse rate or in addition to the natural pulse rate. Artificial excitations have the added benefit that the excitations introduced are introduced at known frequencies. Thus, it is not necessary to first determine the pulse rate of an individual.

However, the movement required to generate the artificial pulse can cause movement of the sensor relative to the patient, introducing the variable of distance into denoising equations for the resultant sensor data. For example, the artificial pulse can dislodge the sensor 300 from the patient measurement site or misalign the measurement site with the emitter and detector of the sensor 300. Accordingly, sensor data from active pulse sensors typically is filtered to determine probe off and probe on conditions, where probe on conditions indicate reliable sensor data and probe off conditions include their ordinary broad meaning known to one of skill in the art, including designating improper application of an optical probe to a measurement site, for example due to movement of the sensor relative to the patient caused by artificial pulsing.

Data from the proximity sensor 355 within the sensor 300 can be used instead of or in addition to more complex data processing methods to determine a probe off condition due to improper alignment of the measurement site and the sensor. For example, if data from the proximity sensor 355 indicates that the measurement site is not properly aligned with the sensor 300, then the sensor 300 can determine a probe off condition for the duration of such data from the proximity sensor 335. Accordingly, data from proximity sensor 355 can provide a computationally simple and accurate means for determining the probe off condition.

In some embodiments, instead of or in addition to using proximity data to determine a probe off condition, data from the proximity sensor 355 can be used to generate a confidence value indicating potential accuracy of measurement data, e.g., plethysmographic data output by a pulse oximeter. For example, during operation a sensor can supply associated proximity data and plethysmographic data to a patient monitor without utilizing probe-off detection or probe repositioning. The patient monitor can then determine a confidence value for each portion of the plethysmographic data based on the associated proximity data, for example a measured distance between a fingertip and a capacitive proximity sensor measured at substantially the same time as when the plethysmographic data was captured. Using the confidence values for the plethysmographic data (e.g., to discard certain portions of the plethysmographic data or to assign different weights to different portions of the plethysmographic data), the patient monitor can estimate pulse rates, respiration rates, and the like for the patient.

Figure 4:
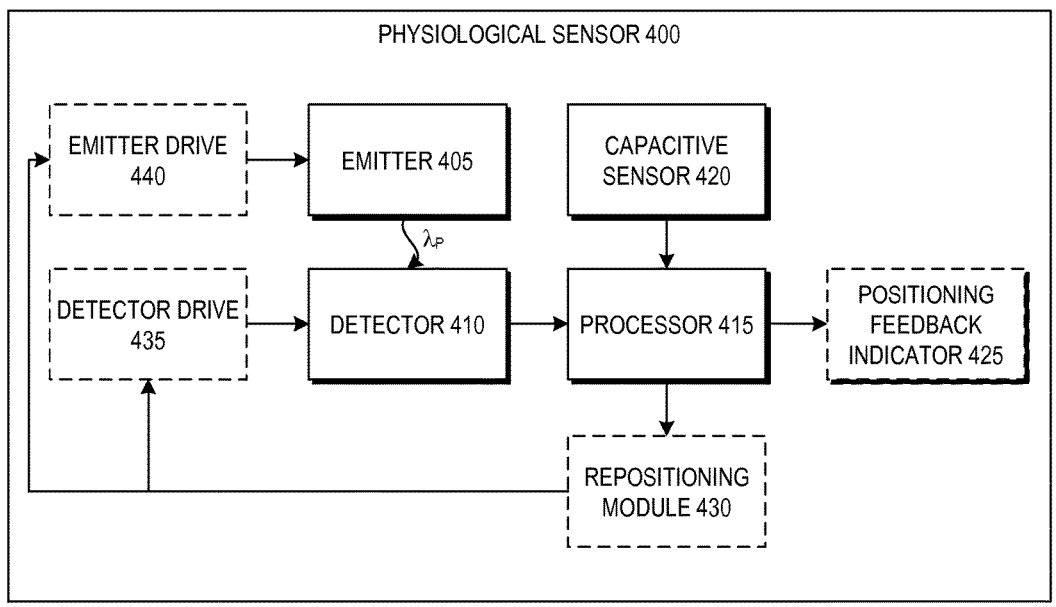
FIG. 4 illustrates a high-level schematic block diagram of an embodiment of a physiological sensor having proximity sensing capabilities.

FIG. 4 illustrates a high-level schematic block diagram of an embodiment of a physiological sensor 400 having proximity sensing capabilities. The physiological sensor 400 includes an emitter 405, detector 410, processor 415, and capacitive sensor 420. In other embodiments the capacitive sensor 420 can be replaced or supplemented by the other types of proximity sensors discussed herein. Various embodiments of the sensor 400 can also include one or more of a set of optional components such as positioning feedback indicator 425, repositioning module 430, emitter drive 440, or detector drive 435. Though not illustrated, the sensor 400 can also include memory, a display, connection ports, user interface elements, alarms, and other components.

The emitter 405 can be capable of emitting light at one or a plurality of wavelengths $\lambda_P$ for noninvasive measurement of constituents of blood flowing within the tissue of a patient measurement site. The emitter 405 and detector 410 can be aligned so that some or all of the light $\lambda_P$ is incident on detector 410 after passage through the measurement site and attenuation by the constituents of the blood.

Intensity signals representing the light $\lambda_P$ incident on detector 410 can be sent to processor 415. Processor 415 can analyze the intensity signals and determine one or more physiological parameter values. For example, processor 415 can calculate a ratio of detected red and infrared intensities, and an arterial oxygen saturation value is empirically determined based on that ratio. Processor 415 can also perform noise filtering on the raw intensity signal data, and can determine probe off and probe on conditions for purposes of excluding unreliable data from use in calculating physiological parameters. Data from the capacitive sensor 420 can provide feedback regarding the distance of a patient measurement from the capacitive sensor, which can be compared to a threshold to determine whether the sensor and finger are improperly aligned. The determination of improper alignment can be used by the processor 415 in one embodiment to determine a probe off condition.

In some embodiments, the processor 415 can generate a repositioning signal based at least partly on the determination of improper alignment from capacitive sensor data. This signal can be sent, in one embodiment, to positioning feedback indicator 425. Positioning feedback indicator 425 can provide visual, audible, or tactile feedback to a user of sensor 400 to indicate whether the sensor should be repositioned. For example, sensor 400 may emit a beep or audible alarm when the sensor 400 is improperly positioned. Sensor 400 may also include one or more visual indications, for example LED lights, that can be used to provide positioning feedback to the user. For instance, a green light may be illuminated to indicate to the user that the sensor 400 is properly positioned. A red light may be illuminated to indicate to the user that sensor 400 is improperly positioned. As another example, sensor 400 may output text or voice commands indicating how far the user must adjust the sensor 400 in order to achieve proper alignment based on the proximity sensor data. Positioning feedback indicator 425 can provide an initial positioning indication when the user first applies the sensor in one embodiment. In some embodiments, positioning feedback indicator 425 can periodically or continuously output positioning feedback to the user, for example for active pulse sensors introducing an artificial pulse during measurement.

The repositioning signal can be sent, in another embodiment, to repositioning module 430. Repositioning module 430 can use the repositioning signal to generate instructions for mechanical repositioning of the emitter 405 and detector 410, for example using emitter drive 440 and detector drive 435. In some embodiments, emitter drive 440 and detector drive 435 could be implemented together as a single optical assembly drive. Emitter drive 440 and detector drive 435 can be used to reposition the emitter 405 and detector 410, respectively, according to the data provided by the capacitive sensor 420 in order to align the emitter 405 and detector 410 with the measurement site.

As discussed above with respect to the sensors of FIGS. 1A-3B, the capacitive sensor 420 can be placed within the body of the sensor 400 to gauge longitudinal displacement of a patient's finger relative to the sensor 400 and, more specifically, the optical assembly including the emitter 405 and detector 410. In some embodiments, multiple capacitive sensors can be positioned along a longitudinal axis of the sensor 400 for additional data as the patient's finger moves within the sensor housing.

III. Overview of Example Capacitive Proximity Sensor

Figure 5:
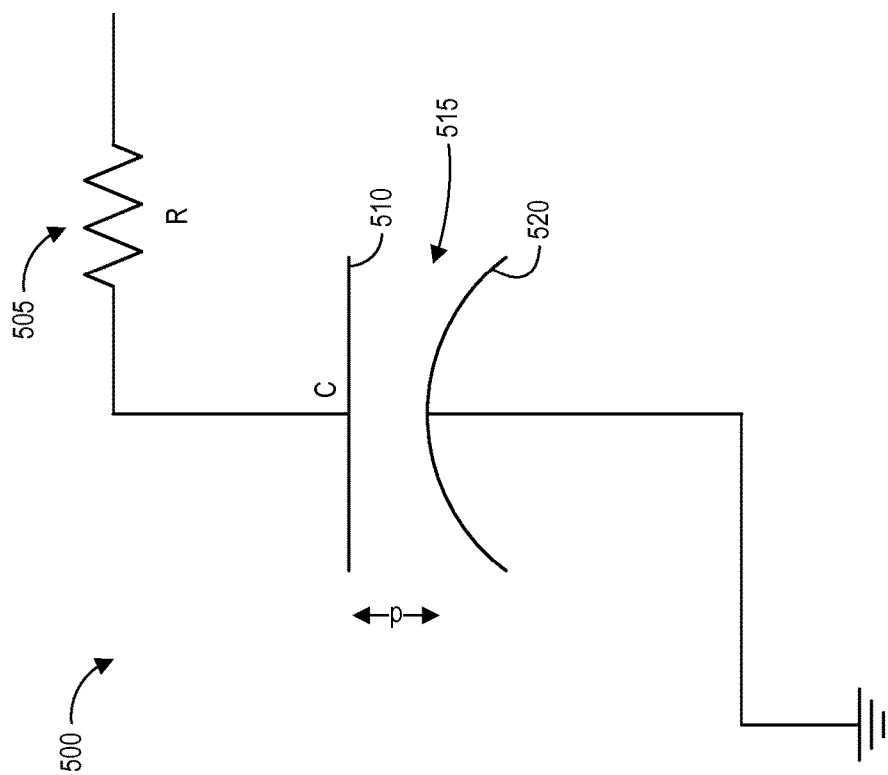
FIG. 5 illustrates a schematic diagram of an embodiment of a circuit for measuring proximity of a measurement site to a sensor.

FIG. 5 illustrates a schematic diagram of an embodiment of a circuit 500 that can be used to determine proximity of a patient measurement site to a physiological sensor. The circuit includes a capacitor 515 and a resistor 505. Here the capacitance, C, can be calculated according to Equation (1), below:

$$C \propto \frac{A}{d} \quad (1)$$

where the capacitance, C, is proportional to the area, A, of the capacitor divided by the distance, d, between the capacitor plates. The capacitor 515 has two plates 510, 520. The first capacitive plate 510 is integrated or connected to the physiological sensor, for example a physical stop near the hinge of the housing of clip-type pulse oximeter, or in an array along the longitudinal axis of the surface of a finger bed of clip-type pulse oximeter. The second capacitor plate 520 is the skin surface of the patient measurement site, with the assumption that the patient is a capacitor. A typical adult has a capacitance of about 120 pF, however capacitance of different people will vary. Accordingly, the distance, d, between the capacitor plates 510, 520 represents the distance between the location of the capacitive sensor within the physiological sensor and the surface of the patient measurement site. In order to obtain the value of the distance, d, from Equation (1), the values of both the capacitance, C, and the area, A, must be known. The area can be predetermined based on the dimensions of the first capacitive plate 510.

The capacitance can be determined from the value of the resistance, R, of the resistor 505 and the value of a time constant, τ, of the circuit 500. The time constant of the circuit 500 can be calculated according to Equation (2), below:

$$\tau = RC \quad (2)$$

where the time constant, τ, is equal to the resistance, R, times the capacitance, C. Hence, the distance, d, between the capacitor plates 510, 520 can be calculated through the combination of Equations (1) and (2) through the measurement of the circuit time constant. Accordingly, as a distance between a patient measurement site, such as a digit of a hand, and the capacitor plate 510 decreases, the time constant τ increases and the capacitance C increases.

In one embodiment, the time constant τ can be determined from the time required to trip a set voltage level, such as about 2.2 volts, given a power supply of known power, such as about 3.3 volts. Although not illustrated, a processor or microprocessor can be in communication with the circuit 500 to measure the time constant. The determined time constant τ can be used to calculate the capacitance, C, using Equation (2). The capacitance C can then used to calculate the distance or relative distance through Equation (1). Accordingly, as a distance between a patient measurement site, such as a digit of a hand, and the capacitor plate 510 decreases, the time constant τ increases and the capacitance C increases.

The value of the distance d can be used to provide a repositioning indication to the patient or physician, to mechanically reposition the optical assembly of an oximeter sensor, or to determine a probe off condition for removing potentially unreliable data from a physiological measurement data set. In some embodiments, a number of circuits 500 can be provided within an oximeter for precise determination of longitudinal displacement of a patient finger within the oximeter housing. Accordingly, at least one of the repositioning indication, optical assembly repositioning, or probe off can be based on a number of distance values corresponding to each of the circuits. Although an example capacitive circuit 500 is depicted, this is for purposes of illustration and in other embodiments other capacitive circuit arrangements can be used. For example, other suitable circuits can include amplifiers, additional resistors, and other elements, for instance to amply the signal to noise and to minimize changes to capacitance based on environmental changes.

IV. Overview of Example Proximity-Sensing Physiological Monitoring Processes

Figure 6:
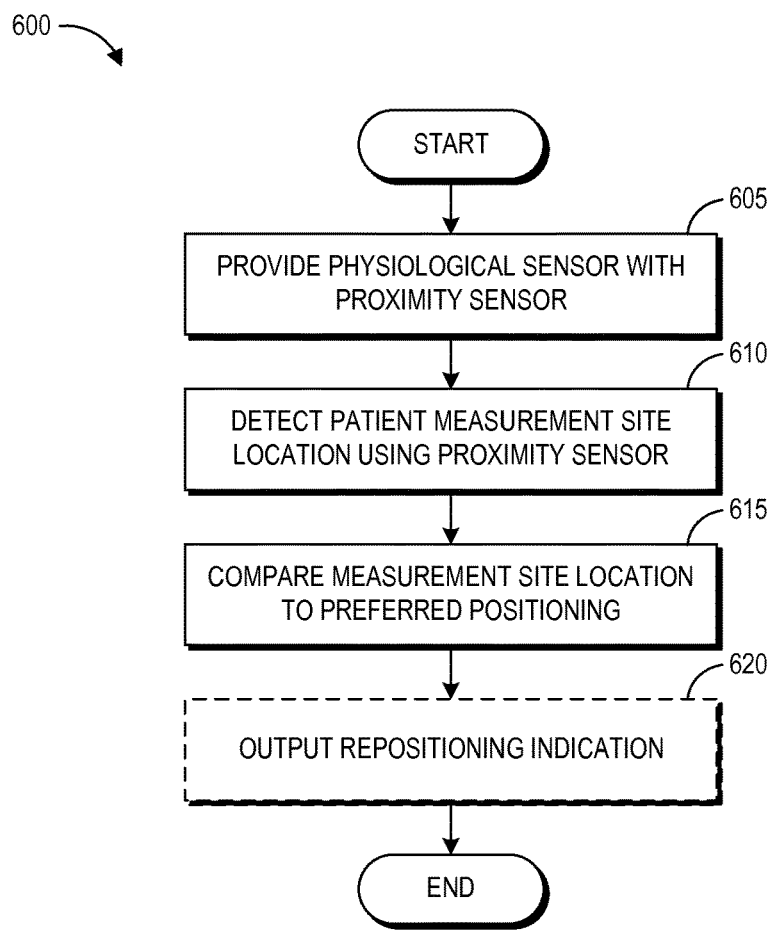
FIG. 6 illustrates an example process for determining positioning during sensor application.

FIG. 6 illustrates an example process 600 for determining positioning during sensor application. The process 600 can be implemented on any physiological sensor including proximity sensing capabilities, for example the physiological sensors illustrated in FIGS. 1A-FIG. 4.

At block 605, a physiological sensor is provided with at least one proximity sensor. For example, one proximity sensor or an array of proximity sensors can be provided including capacitive, optical, electrical, or mechanical proximity sensors, or a combination thereof. The proximity sensor can be configured to determine distance or contact between a measurement site and itself, and can be positioned within the sensor so as to provide feedback regarding alignment of the measurement site and optical components of the sensor.

At block 610, the patient measurement site location is detected using the proximity sensor. For example, using a capacitive proximity sensor, a distance between a capacitive plate in the sensor and the capacitive skin of the patient can be determined. An optical scanning proximity sensor can also determine a distance between the sensor and a patient measurement site. In another example, using a mechanical contact proximity sensor, it can be determined whether the patient measurement site has contacted the mechanical contact proximity sensor, such as by depressing a button.

At block 615, the measurement site location can be compared to preferred positioning. The preferred positioning can include a range of placements relative to the optical components of the sensor that are likely to produce clinically accurate physiological measurements. To illustrate, if a capacitive proximity sensor is used on a physical stop in a pulse oximeter finger clip sensor such as is depicted in FIG. 2A, 2B, 3A, or 3B, a distance of approximately 4 mm-10 mm between the capacitive proximity sensor and the patient fingertip can correspond to proper positioning of an adult finger with respect to an LED emitter and detector. In one embodiment, a distance of approximately 6 mm between the capacitive sensor and the fingertip can indicate preferred positioning of the finger within the sensor. Other ranges can be used to indicate preferred placement in other sensor configurations, for other finger sizes, or for other measurement sites.

At block 620, the sensor can optionally cause the sensor to output a repositioning indication. For instance, in one embodiment of a pulse oximeter finger clip sensor such as is depicted in FIG. 2A, 2B, 3A, or 3B having a capacitive sensor on a physical stop, if the capacitive proximity sensor data indicates that the patient fingertip is closer than approximately 4 mm to the capacitive sensor or farther than approximately 10 mm from the capacitive sensor, the sensor may output a repositioning indication. In some embodiments, the sensor may output a first positioning indication when the sensor is correctly positioned and may output a second positioning indication when the sensor is incorrectly positioned. The second positioning indication may be a visual, auditory, or tactile signal alerting the user that the sensor is incorrectly positioned, and in one example may include specific instructions regarding how to reposition the sensor for proper placement.

Process 600 can be implemented when a user first applies a sensor to a measurement site to indicate proper positioning. In some embodiments, blocks 610-620 may be repeated one or more times during measurement to gauge whether the sensor positioning continues to be proper or whether the sensor should be repositioned. Repetition of this measurement site location detection and comparison portion of process 600 can be beneficial, in one example, in active pulse oximeters that introduce an artificial pulse to a measurement site and therefore possibly introduce movement of the sensor relative to the measurement site. Repetition of blocks 610-620 can also be beneficial, in another example, in patient monitoring situations in which the patient can move during the time in which the sensor is worn and therefore may dislodge the sensor.

Figure 7:
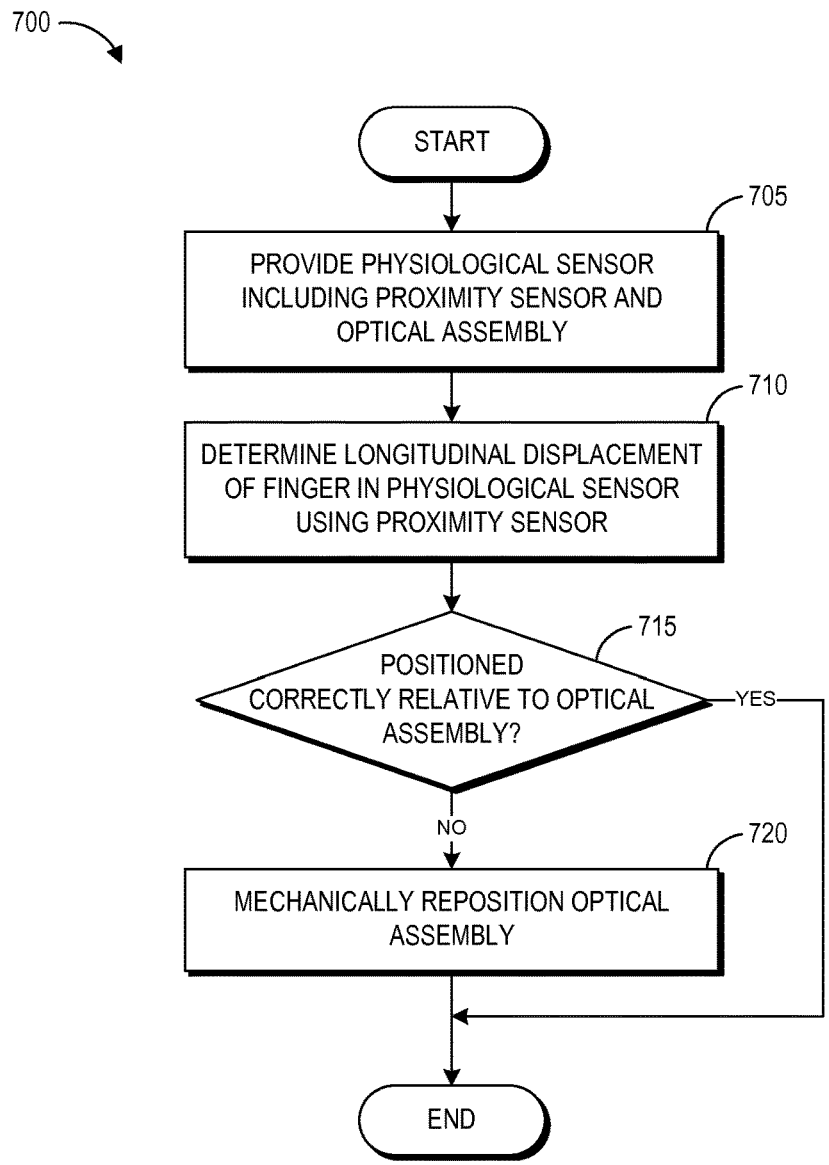
FIG. 7 illustrates an example process for repositioning an applied sensor based on proximity sensing.

FIG. 7 illustrates an example process 700 for repositioning an applied sensor based on proximity sensing. The process 700 can be implemented by the components of any physiological sensor including proximity sensing capabilities, for example the physiological sensors illustrated in FIGS. 1A-FIG. 4.

At block 705, a physiological sensor is provided with at least one proximity sensor. For example, one proximity sensor or an array of proximity sensors can be provided including capacitive, optical, electrical, or mechanical proximity sensors, or a combination thereof. The proximity sensor can be configured to determine distance or contact between a measurement site and itself, and can be positioned within the sensor so as to provide feedback regarding alignment of the measurement site and optical components of the sensor. The physiological sensor also includes an optical assembly, for instance an aligned emitter and detector as discussed above with respect to FIGS. 1A-FIG. 4, for generating intensity signals from which to determine physiological signals.

At block 710, the sensor determines longitudinal displacement of a patient finger in the physiological sensor using the proximity sensor. Many pulse oximeters are contoured to naturally center a patient finger within the sensor, and therefore the proximity sensing discussed herein focuses primarily on determining longitudinal displacement. However, in other sensor embodiments displacement of the measurement site along a vertical or horizontal axis of the sensor may alternatively or additionally be determined. For example, using a capacitive proximity sensor, a distance between a capacitive plate in the sensor and the capacitive skin of the patient can be determined. An optical scanning proximity sensor can also determine a distance between the sensor and a patient measurement site. In another example, using a mechanical contact proximity sensor, it can be determined whether the patient measurement site has contacted the mechanical contact proximity sensor, such as by depressing a button.

At block 715, the sensor determines whether it the patient measurement site is correctly positioned relative to the optical assembly based on the proximity sensor data. As discussed above, for capacitive proximity sensors the distance between the capacitive proximity sensor and the skin of the measurement site can be compared to a threshold or to a range of acceptable positions to determine whether the measurement site is correctly positioned. For a mechanical contact sensor producing a binary contact or no contact output, the correct positioning determination may be made based on the binary output.

If the measurement site is positioned correctly relative to the optical assembly, then the process 700 ends. If the measurement site is not positioned correctly relative to the optical assembly, then the process 700 transitions to block 720 in which the sensor mechanically repositions the optical assembly to achieve proper alignment with the measurement site. For example, capacitive sensing data can be used to determine a distance to mechanically move the optical assembly along the longitudinal axis of the sensor.

Figure 8:
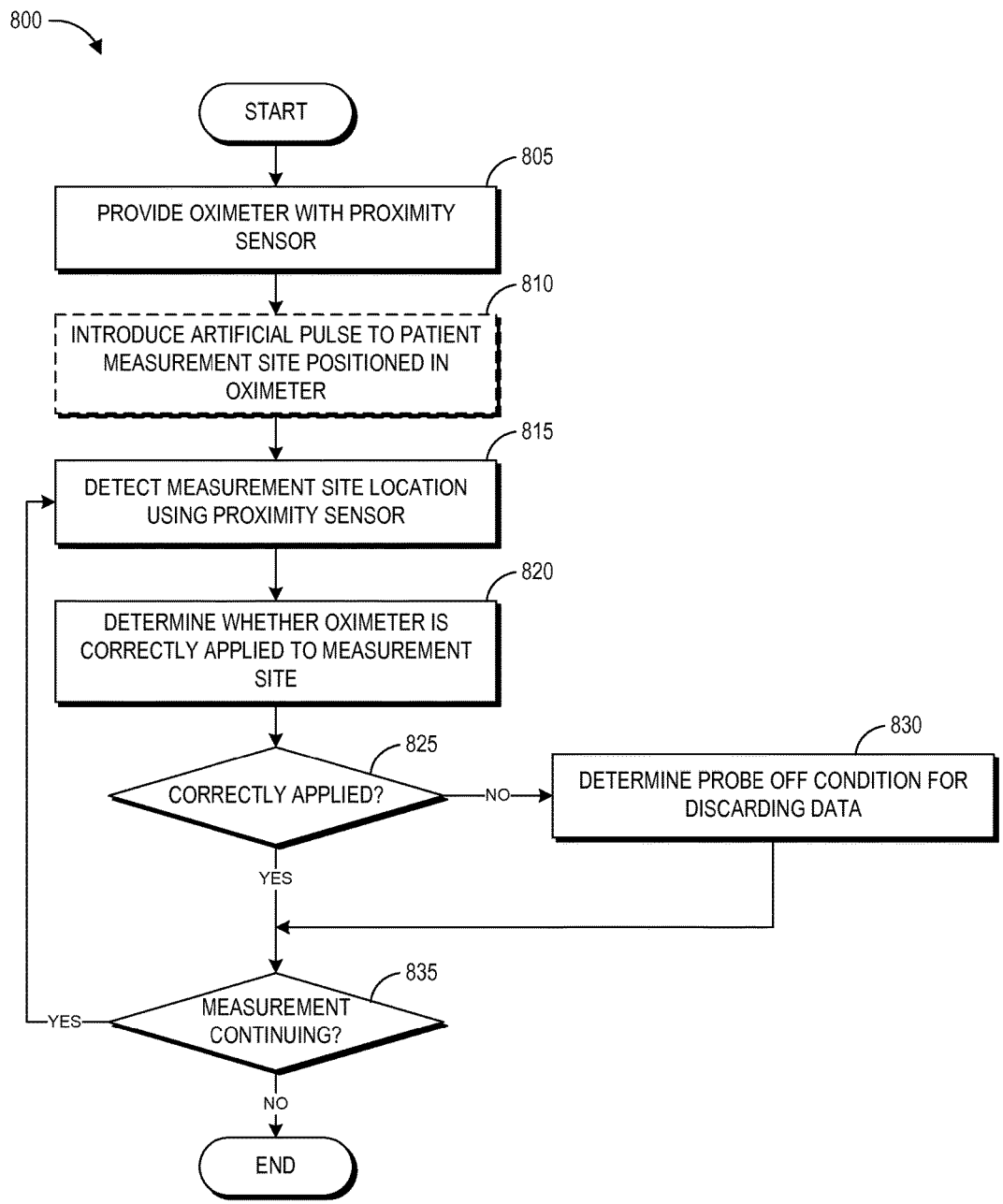
FIG. 8 illustrates an example process for determining a probe off condition based on proximity sensing.

FIG. 8 illustrates an example process 800 for determining a probe off condition based on proximity sensing. The process 800 can be implemented by the components of any physiological sensor including proximity sensing capabilities, for example the physiological sensors illustrated in FIGS. 1A-FIG. 4. Some embodiments of process 800 can be implemented on an active pulse sensor capable of introducing an artificial pulse into a measurement site.

At block 805, a physiological sensor is provided with at least one proximity sensor. For example, one proximity sensor or an array of proximity sensors can be provided including capacitive, optical, electrical, or mechanical proximity sensors, or a combination thereof. The proximity sensor can be configured to determine distance or contact between a measurement site and itself, and can be positioned within the sensor so as to provide feedback regarding alignment of the measurement site and optical components of the sensor.

At block 810, the sensor optionally introduces an artificial pulse to the patient measurement site, such as a finger positioned within a pulse oximeter. As discussed above, the artificial pulse can assist in obtaining more reliable measurement data, however it can also cause movement of the sensor relative to the measurement site, thereby affecting proper positioning of the sensor on the measurement site.

At block 815, the patient measurement site location is detected using the proximity sensor. As discussed above, in some embodiments of a finger clip pulse oximeter the sensor may be placed on a physical stop, and may be oriented to determine longitudinal displacement of the patient finger within the sensor relative to the optical assembly. In one example, using a capacitive proximity sensor, a distance between a capacitive plate in the sensor and the capacitive skin of the patient can be determined. An optical scanning proximity sensor can also determine a distance between the sensor and a patient measurement site. In another example, using a mechanical contact proximity sensor, it can be determined whether the patient measurement site has contacted the mechanical contact proximity sensor, such as by depressing a button.

At block 820, the measurement site location can be compared to preferred positioning data to determine whether the oximeter is correctly applied to the measurement site. Preferred positioning data can be stored in memory of the oximeter, for example a read-only memory (ROM). The preferred positioning can include a range of placements relative to the optical components of the sensor that are likely to produce clinically accurate physiological measurements. In one embodiment, if a capacitive proximity sensor is used on a physical stop in a pulse oximeter finger clip sensor such as is depicted in FIG. 2A, 2B, 3A, or 3B, a distance of approximately 4 mm-10 mm between the capacitive proximity sensor and the patient fingertip can correspond to proper positioning of an adult finger with respect to an LED emitter and detector. As an example, a distance of approximately 6 mm between the capacitive sensor and the fingertip can indicate preferred positioning of the finger within the sensor. As discussed above, other ranges can be used to indicate preferred placement in other sensor configurations, for other finger sizes, or for other measurement sites.

At block 825, the sensor determines based on the comparison of block 810 whether the oximeter is correctly applied to the measurement site. If the sensor is not correctly applied, then the process 800 transitions to block 830 in which the sensor, for example a processor of the sensor or a processor of another device connected to and receiving data from the sensor, determines a probe off condition for discarding the data taken while the sensor was not correctly applied. In some embodiments, a default may be to determine a probe on condition for including data, and data may only be discarded when a probe off condition is determined for a time or range of times during which sensor data was gathered at improper positioning.

After determining the probe off condition at block 830, or if the sensor is determined at block 825 to be correctly applied, the process 800 transitions to block 835 to determine whether measurement is continuing. If measurement continues, then the process 800 loops back to block 815 to determine the measurement site location and to repeat blocks 820 and 825. Once measurement has concluded, for instance when the sensor is powered off or if the sensor detects that the patient measurement site is no longer at least partially within the sensor housing, then the process 800 ends.

V. Terminology

Although many of the examples discussed herein are in the context of pulse oximetry, this is for illustrative purposes only. The sensors, signal conditioning techniques, and proximity sensing applications discussed herein can be adapted for other physiological sensors monitoring other physiological parameters or multiple physiological parameters.

Many other variations than those described herein will be apparent from this disclosure. For example, depending on the embodiment, certain acts, events, or functions of any of the algorithms described herein can be performed in a different sequence, can be added, merged, or left out all together (e.g., not all described acts or events are necessary for the practice of the algorithms). Moreover, in certain embodiments, acts or events can be performed concurrently, e.g., through multi-threaded processing, interrupt processing, or multiple processors or processor cores or on other parallel architectures, rather than sequentially. In addition, different tasks or processes can be performed by different machines and/or computing systems that can function together.

The various illustrative logical blocks, modules, and algorithm steps described in connection with the embodiments disclosed herein can be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be a controller, microcontroller, or state machine, combinations of the same, or the like. A processor can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor can also include primarily analog components. For example, any of the signal processing algorithms described herein can be implemented in analog circuitry. A computing environment can include any type of computer system, including, but not limited to, a computer system based on a microprocessor, a mainframe computer, a digital signal processor, a portable computing device, a personal organizer, a device controller, and a computational engine within an appliance, to name a few.

The steps of a method, process, or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of non-transitory computer-readable storage medium, media, or physical computer storage known in the art. An exemplary storage medium can be coupled to the processor such that the processor can read information from, and write information to, the storage medium. In the alternative, the storage medium can be integral to the processor. The processor and the storage medium can reside in an ASIC. The ASIC can reside in a user terminal. In the alternative, the processor and the storage medium can reside as discrete components in a user terminal.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments of the inventions described herein can be embodied within a form that does not provide all of the features and benefits set forth herein, as some features can be used or practiced separately from others. It should be emphasized that many variations and modifications may be made to the above-described embodiments, the elements of which are to be understood as being among other acceptable examples. All such modifications and variations are intended to be included herein within the scope of this disclosure and protected by the following claims.

What is claimed is:

1. A physiological monitoring system comprising:
    an optical assembly including an emitter configured to at least emit light at one or more wavelengths when in use and a detector aligned with the emitter to detect at least a portion of the light, the detector configured to at least generate intensity signals representing detected light when in use;
    a sensor housing configured to at least accept a measurement site of a patient, the sensor housing comprising:
        a first housing component including the emitter,
        a second housing component including the detector, and
        a proximity sensor positioned on one or both of the first housing component and the second housing component; and
    a processor configured to at least:
        receive data from the proximity sensor representing positioning of the measurement site relative to the proximity sensor,
        based at least partly on the data from the proximity sensor, determine that a distance between the proximity sensor and the measurement site does not correspond to correct positioning of the measurement site relative to the emitter and the detector, and
        based at least partly on the distance, generate instructions for at least one drive to reposition one or both of the emitter and detector to align with the measurement site.

2. The system of claim 1, wherein the proximity sensor comprises a capacitor.

3. The system of claim 2, wherein the proximity sensor is configured to generate capacitive sensor data representing a distance between the measurement site and the proximity sensor.

4. The system of claim 3, wherein the processor is configured to determine the positioning of the measurement site relative to the emitter and the detector based at least partly on the distance between the measurement site and the proximity sensor.

5. The system of claim 1, the second housing component comprising a physical stop positioned to contact the measurement site when inserted into the sensor housing and configured to assist in positioning the measurement site relative to the detector.

6. The system of claim 5, wherein the proximity sensor is also located along a surface of the physical stop.

7. The system of claim 1, the second housing component comprising a finger bed including a generally curved surface shaped generally to receive the measurement site, the finger bed including an aperture over the detector.

8. The system of claim 7, further comprising a plurality of proximity sensors positioned in an array along a longitudinal axis of the finger bed.

9. The system of claim 1, wherein the proximity sensor comprises one or more of an optical, mechanical, or electrical sensor configured to interface with skin of a measurement site.

10. The system of claim 1, wherein the processor is further configured to:
    determine improper alignment of the measurement site and detector based at least partly on the distance; and
    generate a repositioning signal indicating that the measurement site should be repositioned within the sensor housing.

11. The system of claim 10, wherein the processor is configured to generate the instructions for the at least one drive based at least partly on the repositioning signal.

12. The system of claim 1, further comprising the at least one drive, wherein the at least one drive is configured for mechanically repositioning the one or both of the emitter and the detector along a longitudinal axis of the sensor housing based at least partly on the instructions.

13. The system of claim 1, wherein the processor is configured to compare the positioning of the measurement site relative to the emitter and the detector to a preferred positioning.

14. The system of claim 13, wherein the processor is configured to determine improper alignment based at least partly on comparing the positioning of the measurement site relative to the optical assembly to the preferred positioning.

15. The system of claim 14, wherein the processor is configured to determine a probe off condition based on the improper alignment, and to discard any data obtained from the detector during persistence of the probe off condition.

16. The system of claim 1, wherein the processor is configured to determine one or more physiological parameter values based on the positioning of the measurement site relative to the emitter and the detector and on the intensity signals received from the detector.

17. The system of claim 16, wherein the processor is configured to generate a confidence value for each portion of the intensity signals received from the detector based on corresponding data received from the proximity sensor.

18. The system of claim 17, wherein, to determine the one or more physiological parameter values, the processor is configured to discard or assign a weight to each portion of the intensity signals received from the detector based on the associated confidence value.

\* \* \* \* \*